United States Patent
Kaushik et al.

(10) Patent No.: US 11,111,425 B2
(45) Date of Patent: Sep. 7, 2021

(54) METHODS AND SYSTEM TO REDUCE IMPERCEPTIBLE LAB EXPERIMENTS

(71) Applicant: Schlumberger Technology Corporation, Sugar Land, TX (US)

(72) Inventors: Bhanu Kaushik, Stafford, TX (US); Samir Menasria, Missouri City, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 912 days.

(21) Appl. No.: 15/187,138

(22) Filed: Jun. 20, 2016

(65) Prior Publication Data
US 2017/0364607 A1    Dec. 21, 2017

(51) Int. Cl.
| | | |
|---|---|---|
| C09K 8/00 | (2006.01) | |
| C09K 8/42 | (2006.01) | |
| G06N 7/00 | (2006.01) | |
| G16C 20/30 | (2019.01) | |

(52) U.S. Cl.
CPC .................. *C09K 8/00* (2013.01); *C09K 8/42* (2013.01); *G06N 7/00* (2013.01); *G16C 20/30* (2019.02)

(58) Field of Classification Search
CPC ....................................................... G16B 5/00
See application file for complete search history.

(56) References Cited

U.S. PATENT DOCUMENTS

| | | | | |
|---|---|---|---|---|
| 5,446,681 | A * | 8/1995 | Gethner | G01N 21/359 702/27 |
| 2009/0277640 | A1* | 11/2009 | Thompson | C09K 8/68 166/305.1 |
| 2013/0220607 | A1* | 8/2013 | Phatak | E21B 33/10 166/279 |
| 2018/0135382 | A1* | 5/2018 | Jandhyala | C09K 8/42 |

* cited by examiner

*Primary Examiner* — Daniel T Pellett

(57) ABSTRACT

Methods may include defining operational parameters for an initial composition design; generating an initial composition design from the defined operational parameters; predicting the performance of the initial composition design using a statistical model; comparing the performance of the initial composition design with the operational parameters; optimizing the initial composition design according to the defined operational parameters; and outputting a final composition design. Methods may also include defining operational parameters for an initial composition design for a wellbore fluid; generating an initial composition design from the defined operational parameters; predicting the performance of the initial composition design using a statistical model; comparing the performance of the initial composition design with the operational parameters; optimizing the initial composition design according to the defined operational parameters; and outputting a final composition design.

19 Claims, 3 Drawing Sheets

METHODS AND SYSTEM TO REDUCE IMPERCEPTIBLE LAB EXPERIMENTS

BACKGROUND

Customized chemical composition formulation based on a defined need is a complex and time consuming task on the commercial scale. For example, in standard practice a requirement for a particular composition is set based upon client preferences and the demands of the operational environment. However, composition design may also be constrained in some cases by additional considerations that may include, for example, the availability of composition components within a geographical region or governmental restrictions for operating in environmentally sensitive areas. Following the initial stage, the standard optimization process for a composition often involves a laboratory technician relying on experience and empirical data to develop a composition that performs in agreement with client operational requirements. Composition designs are then validated in a laboratory through various experiments to verify that all design criteria are satisfied. Numerous experiments are often conducted.

SUMMARY

This summary is provided to introduce a selection of concepts that are described further below in the detailed description. This summary is not intended to identify key or essential features of the claimed subject matter, nor is it intended to be used as an aid in limiting the scope of the claimed subject matter.

In one aspect, embodiments of the present disclosure are directed to methods that include defining operational parameters for an initial composition design; generating an initial composition design from the defined operational parameters; predicting the performance of the initial composition design using a statistical model; comparing the performance of the initial composition design with the operational parameters; optimizing the initial composition design according to the defined operational parameters; and outputting a final composition design.

In another aspect, embodiments of the present disclosure are directed to methods that include defining operational parameters for an initial composition design for a wellbore fluid, wherein the operational parameters comprise one or more selected from a group consisting of wellbore geometry, formation composition, environmental variables, composition components, pricing information, and temperature; generating an initial composition design from the defined operational parameters; predicting the performance of the initial composition design using a statistical model; comparing the performance of the initial composition design with the operational parameters; optimizing the initial composition design according to the defined operational parameters; and outputting a final composition design.

Other aspects and advantages of the disclosure will be apparent from the following description and the appended claims.

DETAILED DESCRIPTION

In one aspect, methods in accordance with this disclosure are directed to design processes to reduce the number of laboratory tests required during the development of customized composition designs that perform according to the specifications of a particular job or client. Methods may utilize a software platform that allows a user to select and optimize composition designs and perform evaluations for expected behavior for various composition components and concentration ranges prior to performing experiments on the actual composition design. In one or more embodiments, methods may include a user-guided application that utilizes computer modeling and statistical algorithms to generate optimized composition designs based upon defined constraints and historical experimental data.

Methods in accordance with the present disclosure may be used to generate customized compositions tailored to a set of user-defined criteria and obviate the need for, or minimizing the number of, laboratory experiments often used to develop composition designs, which may reduce the need for composition design techniques that involve screening incremental formulation changes, experimentation, and optimization. In one or more embodiments, methods in accordance with the present disclosure may allow a user to predict the outcome of lab experiments without experimentation and to identify compositions suitable for any input parameters. Applications in accordance with the present disclosure may include a user interface that presents a user with a selection of optimized composition designs. In particular embodiments, computer modeling may output a composition design that takes into account user inputs that may include market pricing, material properties, availability, operating conditions, chemical compatibilities, and the like.

In one or more embodiments, custom composition design may involve the use of statistical analytic models that utilize historical laboratory data to predict with defined accuracy the expected outcome of testing methods for composition design candidates. Final compositions designs may then be validated by laboratory experiment in some embodiments, and the experimental data may be compiled into the historical database to reduce the error for future iterations of composition design and improve the predictive quality of the analytical models.

Figure 1:
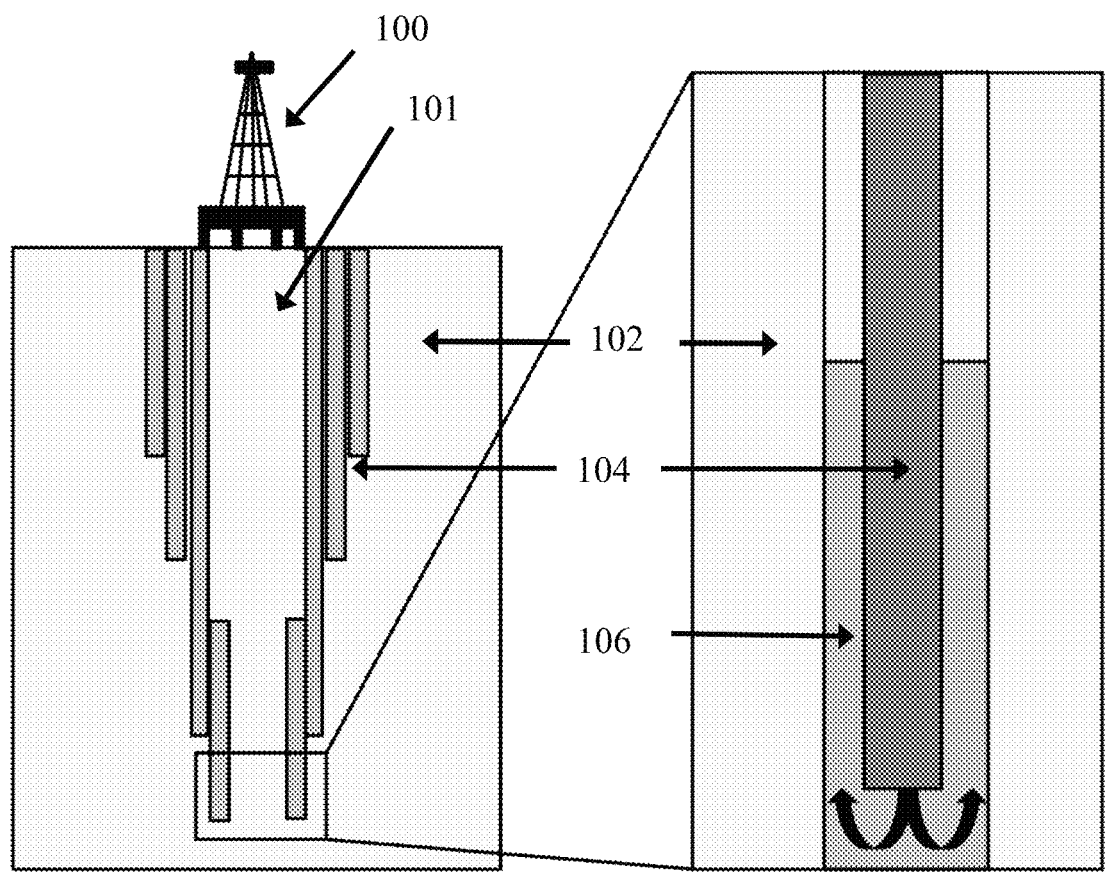
FIG. 1 is an illustration of a completions operation in which cement is installed in an annular region created between a borehole and an installed casing in accordance with embodiments of the present disclosure.

Composition designs may be directed to the production and optimization of cement compositions in some embodiments. Cement compositions may then be emplaced within a wellbore, such as in an annulus created between a wall of the formation and a section of casing installed within the wellbore. With particular respect to FIG. 1, a derrick 100 is shown installed on a wellbore 101 traversing a formation 102. Within the wellbore 101 concentric segments of casing 104 are nested within each other, in preparation for installation of a cement sheath between the outside of the casing and the exposed formation and/or other emplaced casing strings. During the cementing operation, a cement slurry 106 is pumped into an annulus formed between formation 102 and the casing 104. In some embodiments, cement slurry may be pumped into multiple annular regions within a wellbore such as, for example, (1) between a wellbore wall and one or more casing strings of pipe extending into a wellbore, or (2) between adjacent, concentric strings of pipe extending into a wellbore, or (3) in one or more of an A- or B-annulus (or greater number of annuli where present) created between one or more inner strings of pipe extending into a wellbore, which may be running in parallel or nominally in parallel with each other and may or may not be concentric or nominally concentric with the outer casing string.

However, while cementing is presented as a possible embodiment, it is also envisioned that methods of the present disclosure may be applied to other wellbore fluids and to the formulation of composition designs for industrial applications in which historical testing data for a number of formulations is available. Testing data may include data regarding chemical properties and compatibilities, solubility data, crush testing for proppants, fibers, and solid other additives, temperature stability data, data from various laboratory techniques including fluid loss testing, melting and boiling point data, titrations, scratch testing, filter cake formation and breaking data, spurt loss, gravimetric data, crystallization data, rheometry, hardness testing, and the like.

In one or more embodiments, methods in accordance with the present disclosure may be used to formulate wellbore fluids to minimize equipment wear and corrosion, such as the formulation of acid treatments to contain corrosion inhibitors, scale inhibitors, buffering systems, rheology modifiers, chelants, temperature stabilizers, and solvents. In some embodiments, methods in accordance with the present disclosure may be used to formulate wellbore fluids that include fracturing fluids, pads, and spacer fluids used in fracturing operations with control over fluid performance characteristics such as, for example, rheology, friction, fluid loss control, component solubility, proppant content, and leak-off. Further, applications may include design of multi-component compositions used outside of a wellbore including in the transport of hydrocarbon fluids, treatment of waste streams, and development of chemical packages and concentrates for industrial use.

Figure 2:
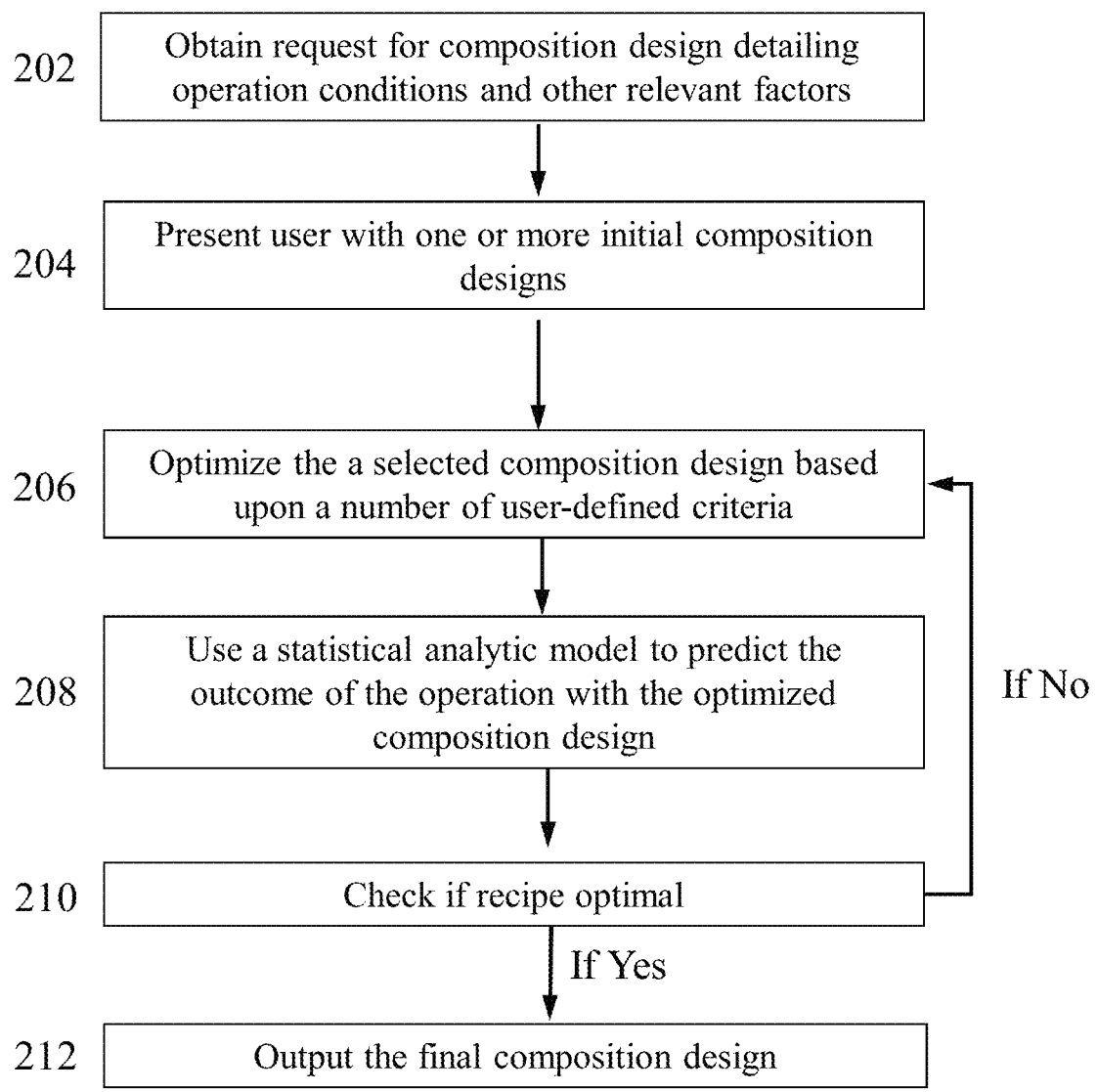
FIG. 2 is a schematic depicting a flow diagram in accordance with embodiments of the present disclosure.

Methods of composition design in accordance with the present disclosure may involve the construction of a model detailing user-specified parameters for a composition design that are tested and screened using a statistical model to generate an optimized final composition design. With particular respect to FIG. 2, a flow diagram is presented showing an embodiment of workflow in accordance with the present disclosure. The method begins at 202 in which a generated request for a customized composition design is used to define the factors relevant for the chemical composition. Design considerations may include the environment in which the composition design will be used, materials that should be used, cost constraints, desired fluid rheology, features for transport to a job site, operating temperature ranges, corrosive properties, toxicity, concentration ranges of composition components, and other relevant characteristics. A user may then select a prospective starting composition design on which to perform an optimization routine at 204. Once a composition design is selected, the composition design is then optimized at 206 according to the input operational parameters.

A statistical analytic model is then used at 208 to perform a number of virtual experiments based on the expected outcome of the composition design when employed in the target environment. A statistical model is built on the historical data using the composition parameters such as blend fluids, chemicals operating parameters such as temperatures, pressure etc. Based on these parameters multiple analytics algorithms are used to generate an ensemble of analytics model which is used later to predict/score jobs. The model may vary the parameters of the composition design to optimize the design depending on a number of factors. For example, a composition design for a wellbore fluid may take into account the concentration of various components within the fluid, the type of job such as completions or drilling, the length of tubing with the well, the depth of the well, the range of operating temperatures, rheology and friction gradients, cost optimizations, and the like. In particular embodiments, composition designs directed to settable compositions, such as cements and polymer-forming compositions, may also take into account the setting or curing time with respect to handling and travel times, and strength and hardness requirements for the final composition design.

Models in accordance with the present disclosure may set up a series of rules and perform experiments or scenarios to analyze composition design performance, generating a composition design that meets the input requirements to a satisfactory degree. Following the modification of the composition design within the user-defined parameters, a final composition design is obtained and output at 210. At this point a user or user-guided program may determine if the recipe is optimal with respect to the input user criteria. If it is determined that the composition design meets the desired criteria to a satisfactory degree, the final composition design is output at 210. If the design composition is unsatisfactory, optimization continues by performing steps 206-210 for one or more iterations until a satisfactory composition design is reached. The final composition design output at 212 may then be used directly or may be validated by laboratory experiment. In one or more embodiments, usage data obtained for the final composition design, in the form of field or experimental data, may be compiled into the historical database and incorporated in future statistical modes.

Methods in accordance with the present disclosure may produce one or more composition designs based on the context of the input requirements from the field. Models in accordance with the present disclosure may be developed using information regarding the individual fluid and solid composition components, and may incorporate optimization routines that allow the input of various operation-specific parameters such as environmental constraints, chemical properties such as setting times or set strength, fluid rheology, pumping schedules, and other variables used to develop an internal set of rules that is used to screen composition components and output a composition design meeting the selected criteria.

In embodiments directed to the design and preparation of wellbore fluid compositions, applications in accordance with the present disclosure may use inputs such as the downhole environment, formation properties, chemical reactivity of various connate fluids, temperatures, and the like, to construct a model for optimizing composition designs. For example, models in accordance with the present disclosure may be a three dimensional (3D) model that estimates properties of the reservoir based on obtained reservoir data. For example, the base model may be a geo-mechanical and material property model of the subsurface of the wellsite and/or the reservoir.

In particular embodiments, design inputs may include wellbore modeling parameters such as vertical stress, pore pressure, horizontal stresses, reservoir porosity, permeability, vertical permeability, lateral permeability, mechanical properties such as Poisson's Ratio, Young's Modulus, and the like. Other inputs may include cost of resources, cost of capital, raw materials, enterprise operations and/or processes, network management, performance, equipment, energy, competitors, marketing, sales, product specifications, geographic location, economic factors, ambient conditions, customer information, environmental information, among others. Design parameters that may be relevant to wellbore fluid compositions may include, for example, the safe mud weight window, cementing weight, and cement type, casing type, production tubing type, perforation method, casing point locations, the cost of the materials to be used, and the like.

Composition designs in accordance with the present disclosure may include predicted compositional properties and performance data generated by an analytical model in some embodiments. In some embodiments, composition designs may also include optimized instructions regarding preparation and use of the composition design depending on the operational requirements. For example, in embodiments directed to wellbore compositions, an output design may include a pumping schedule for a wellbore fluid and/or an order of addition for various components in the design. Further, composition designs may also include estimated chemical and rheological properties, which may enable users to select other operational features such as equipment used in conjunction with the composition such as compatible materials and pumps for transport and handling.

Composition designs in accordance with the present disclosure may include cements and other settable materials. Cement compositions may include mixtures of lime, silica and alumina, lime and magnesia, silica, alumina and iron oxide, materials such as calcium sulphate and Portland cements, and pozzolanic materials such as ground slag, or fly ash. Formation, pumping, and setting of a cement slurry is known in art, and may include the incorporation of cement accelerators, retardants, dispersants, etc., as known in the art, so as to obtain a slurry and/or set cement with desirable characteristics.

In a particular embodiment, cement compositions may incorporate a magnesium-based cement such as a "Sorel" cement. Magnesium-based cements are fast setting cements that approach maximum strength within 24 hours of contact with water. While not limited by any particular theory, the cement-forming reaction mechanism is thought to be an acid-base reaction between a magnesium oxide, such as MgO, and available aqueous salts. For example, mixing solid MgO and a brine containing $MgCl_2$ results in an initial gel formation followed by the crystallization of the gel into an insoluble cement matrix, producing magnesium oxychloride (MOC) cement. Other magnesium-based cements may be formed from the reaction of magnesium cations and a number of counter anions such as, for example, halides, phosphates, sulfates, silicates, aluminosilicates, borates, and carbonates. In some embodiments, anions may be provided by a magnesium salt of the selected anion.

In addition to MOC cements, prominent examples of magnesium-based cements also include magnesium oxysulfate (MOS) cements formed by the combination of magnesium oxide and a magnesium sulfate solution), and magnesium phosphate (MOP) cements formed by the reaction between magnesium oxide and a soluble phosphate salt, such as ammonium phosphate ($NH_4H_2PO_4$). Other suitable magnesium cements may also include magnesium carbonate and magnesium silicate cements. In one or more embodiments, magnesium cements may also include combinations of any magnesium cements described herein and those known in the art.

In other embodiments, the cement composition may be selected from hydraulic cements known in the art, such as those containing compounds of calcium, aluminum, silicon, oxygen and/or sulfur, which set and harden by reaction with water. These include "Portland cements," such as normal Portland or rapid-hardening Portland cement, sulfate-resisting cement, and other modified Portland cements; high-alumina cements, high-alumina calcium-aluminate cements; and the same cements further containing small quantities of accelerators or retarders or air-entraining agents. Other cements may include phosphate cements and Portland cements containing secondary constituents such as fly ash, pozzolan, and the like. Other water-sensitive cements may contain aluminosilicates and silicates that include ASTM Class C fly ash, ASTM Class F fly ash, ground blast furnace slag, calcined clays, partially calcined clays (e.g., metakaolin), silica fume containing aluminum, natural aluminosilicate, feldspars, dehydrated feldspars, alumina and silica sols, synthetic aluminosilicate glass powder, zeolite, scoria, allophone, bentonite and pumice.

In one or more embodiments, the set time of the cement composition may be controlled by, for example, varying the grain size of the cement components, varying the temperature of the composition, or modifying the availability of the water from a selected water source. In other embodiments, the exothermic reaction of components included in the cement composition (e.g., magnesium oxide, calcium oxide) may be used to increase the temperature of the cement composition and thereby increase the rate of setting or hardening of the composition.

Cement compositions may also include a variety of inorganic and organic aggregates, such as saw dust, wood flour, marble flour, sand, glass fibers, mineral fibers, and gravel. In some embodiments, a cement component may be used in conjunction with set retarders known in the art to increase the workable set time of the cement. Examples of retarders known in the art include organophosphates, amine phosphonic acids, lignosulfate salts, hydroxycarboxylic acids, carbohydrates, borax, sodium pentaborate, sodium tetraborate, or boric acid, and proteins such as whey protein.

Figure 3:
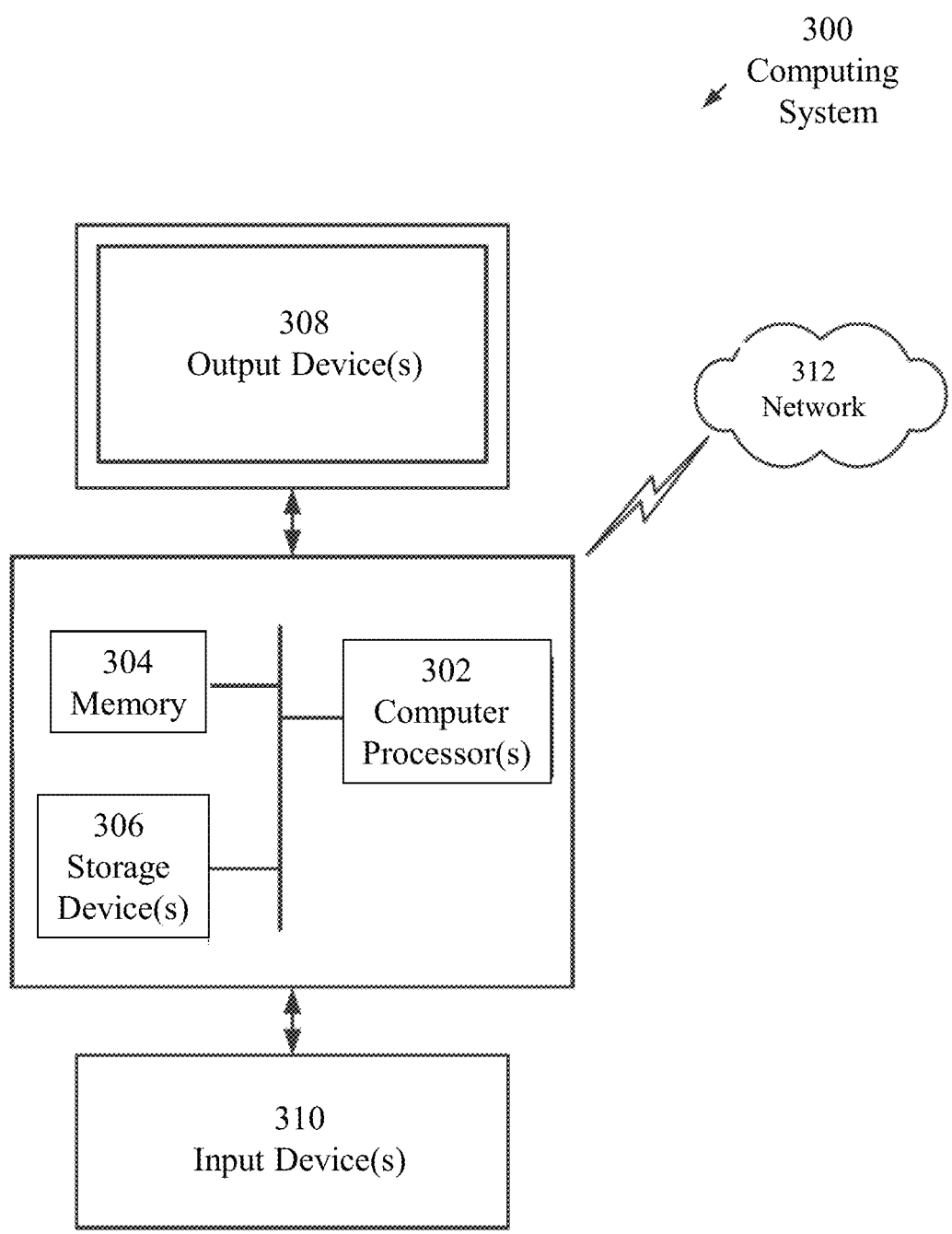
FIG. 3 is a computer system in accordance with embodiments of the present disclosure.

Embodiments of the present disclosure may be implemented on a computing system. Any combination of mobile, desktop, server, embedded, or other types of hardware may be used. For example, as shown in FIG. 3, the computing system (300) may include one or more computer processor(s) (302), associated memory (304) (e.g., random access memory (RAM), cache memory, flash memory, etc.), one or more storage device(s) (306) (e.g., a hard disk, an optical drive such as a compact disk (CD) drive or digital versatile disk (DVD) drive, a flash memory stick, etc.), and numerous other elements and functionalities. The computer processor(s) (302) may be an integrated circuit for processing instructions. For example, the computer processor(s) may be one or more cores, or micro-cores of a processor. The computing system (300) may also include one or more input device(s) (310), such as a touchscreen, keyboard, mouse, microphone, touchpad, electronic pen, or any other type of input device. Further, the computing system (300) may include one or more output device(s) (308), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (300) may be connected to a network (312) (e.g., a local area network (LAN), a wide area network (WAN) such as the Internet, mobile network, or any other type of network) via a network interface connection (not shown). The input and output device(s) may be locally or remotely (e.g., via the network (512)) connected to the computer processor(s) (302), memory (304), and storage device(s) (506). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (300) may be located at a remote location and connected to the other elements over a network (312). Further, embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method comprising:
   defining operational parameters for an initial composition design based on user-specified design considerations including: well environment in which a composition will be used, including wellbore modeling parameters related to vertical stresses, horizontal stresses and permeability; operating temperature ranges; cost constraints; and transport to a wellsite;
   using a three-dimensional model on a computing system having a computer processor to estimate properties of a reservoir based on obtained reservoir data;
   generating an initial composition design based on the defined operational parameters and the three-dimensional model;
   predicting the performance of the initial composition design using a statistical model;
   comparing the performance of the initial composition design with the operational parameters;
   optimizing the initial composition design according to the defined operational parameters by adding at least one of a corrosion inhibitor, a scale inhibitor, a buffering agent, a rheology modifier, a chelant, a temperature stabilizer, or a solvent so as to minimize wear on well equipment located in the well environment;
   further optimizing the initial composition design by iteratively repeating the stages of predicting, comparing, and optimizing; and
   outputting a final composition design suitable for use in a well.

2. The method of claim 1, wherein the operational parameters comprise one or more selected from a group consisting of environmental variables, composition components, and pricing information.

3. The method of claim 1, wherein the statistical model comprises historical data of laboratory results for composition components and prior composition designs.

4. The method of claim 1, wherein the final composition design comprises usage information for the final composition design and/or pricing information.

5. The method of claim 1, further comprising validating the final composition design.

6. The method of claim 1, further comprising predicting the performance of the modified composition design using the statistical model.

7. The method of claim 1, wherein the final composition design comprises one or more selected from a group consisting of composition component concentrations, order of composition component addition, pumping schedule, and reaction times.

8. The method of claim 1, wherein optimizing comprises modifying the initial composition design to generate a modified composition design by adjusting one or more selected from a group consisting of composition component concentration, composition component cost, composition design rheology, and pumping rate.

9. The method of claim 8, further comprising predicting the performance of the modified composition design using the statistical model.

10. The method of claim 1, wherein the initial composition design comprises a composition that hardens to form a polymer or cement, and wherein the operational parameters comprise setting time and/or hardness.

11. A method comprising:
    defining operational parameters for an initial composition design for a wellbore fluid composition, wherein the operational parameters comprise geometry of a wellbore; wellbore modeling parameters related to vertical stresses, horizontal stresses and permeability; environmental variables; composition components pricing information; and temperature;
    generating an initial composition design from the defined operational parameters;
    predicting the performance of the initial composition design using a statistical model;
    comparing the performance of the initial composition design with the operational parameters;
    optimizing the initial composition design according to the defined operational parameters so as to reduce wear and corrosion of well equipment located in the wellbore, the optimization being achieved by using modeling, based on individual fluid and solid components of the initial composition design, which incorporates optimization routines allowing input of operation specific parameters;
    further optimizing the initial composition design by iteratively repeating the stages of predicting, comparing, and optimizing;

using data from a historical database to reduce errors during optimizing the initial composition design;

outputting a final composition design;

validating the final composition design at least in part by laboratory experiment; and compiling experimental data from each laboratory experiment into the historical database.

12. The method of claim 11, wherein the operational parameters further comprise one or more selected from a group consisting of a safe mud weight window, cementing weight, cement type, casing type, production tubing type, perforation method, and casing point locations.

13. The method of claim 11, wherein the operational parameters comprise one or more formation properties selected from a group consisting of vertical stress, pore pressure, horizontal stresses, reservoir porosity, permeability, vertical permeability, lateral permeability, mechanical properties such as Poisson's Ratio, and Young's Modulus.

14. The method of claim 11, wherein the statistical model comprises historical data of laboratory results for composition components and prior composition designs.

15. The method of claim 11, wherein the final composition design comprises usage information for the final composition design and/or pricing information.

16. The method of claim 11, further comprising updating the statistical model to contain data obtained from validating the final composition design.

17. The method of claim 11, wherein the final composition design comprises one or more selected from a group consisting of composition component concentrations, order of composition component addition, pumping schedule, and reaction times.

18. The method of claim 11, wherein optimizing comprises modifying the initial composition design to generate a modified composition design by adjusting one or more selected from a group consisting of composition component concentration, composition component cost, composition design rheology, and pumping rate.

19. The method of claim 11, wherein the initial composition design comprises a composition that hardens to form a polymer or cement, and wherein the operational parameters comprise setting time and/or hardness.

* * * * *